United States Patent [19]
Marcon

[11] Patent Number: 6,029,662
[45] Date of Patent: Feb. 29, 2000

[54] COMPRESSED-AIR POWDER INHALER

[75] Inventor: Christian Marcon, Creteil, France

[73] Assignee: Pierre Fabre Medicament, Boulogne, France

[21] Appl. No.: 09/039,625

[22] Filed: Mar. 16, 1998

[51] Int. Cl.[7] .......................... A61M 15/00; A61M 11/00; A61M 16/00

[52] U.S. Cl. .............. 128/203.15; 128/203.12; 128/200.22; 128/204.26

[58] Field of Search .......... 128/203.12, 203.15, 128/203.21, 200.22, 200.23, 204.26; 604/58

[56] References Cited

U.S. PATENT DOCUMENTS 5,287,850  2/1994  Haber et al. .
5,347,999  9/1994  Poss et al. .
5,388,572  2/1995  Mulhauser et al. .

FOREIGN PATENT DOCUMENTS

0 490 797  of 0000  European Pat. Off. .

*Primary Examiner*—John G. Weiss
*Assistant Examiner*—Todd Martin
*Attorney, Agent, or Firm*—Burns, Doane, Swecker & Mathis, L.L.P.

[57] ABSTRACT

A powder inhaler contains powder and includes a mechanism for providing pressurized gas to discharge the powder through a mouthpiece. The gas must pass through an orifice before reaching the powder. The orifice is normally closed by an obturator which is released in response to the sensing of suction in the mouthpiece. The pressurized gas can bias the obturator to an orifice opening position prior to the detection of suction in the mouthpiece, so that when the obturator is released, the orifice is immediately and rapidly opened, and powder is rapidly emitted through the mouthpiece.

13 Claims, 7 Drawing Sheets

FIG_1

COMPRESSED-AIR POWDER INHALER

BACKGROUND OF THE INVENTION

The invention relates to powder inhalers.

Document EP-0,549,605 B1 discloses a powder inhaler, in particular for medicinal treatment, including an air supply chamber communicating with a conduit leading into a suction mouthpiece. Means is provided for bringing into the conduit, before each use, a dose of powder which is to be inhaled. The air is delivered into the conduit, entrains the powder, passes through the mouthpiece and reaches the user's lungs. The air delivery facilitates the administration of the powder in the lungs without demanding from the user an inspiration effort which said user is sometimes incapable of providing. To ensure that the success of the treatment is optimal, the entire dose of powder must be conveyed deep into the lungs. However, this is only possible if the air is delivered at the exact moment the user inspires. To this end, the inhaler includes a drawer which is slidably movable in the inhalation conduit and sensitive to suction in the mouthpiece. This drawer is connected to a piston of the chamber which it locks in position counter to a compressed return spring. When the patient breathes in, the displacement of the drawer frees the piston, the movement of which generates the flow of air in the conduit for entraining the powder. Thus, the air is delivered in synchronization with the patient's inspiration. However, the mechanism for synchronizing the delivery of the air with the inspiration extends from the conduit as far as the piston and is thus relatively large and complicated.

An object of the invention is to make available a compressed-air powder inhaler which includes a synchronization mechanism of simple structure and of small size which permits instant delivery of air.

SUMMARY OF THE INVENTION

To achieve this object, the invention Provides a powder inhaler Including an air supply chamber, a conduit communicating with the chamber via an orifice and leading into an inhalation mouthpiece, means for bringing a dose of powder into the conduit, and a detector for detecting suction created in the mouth-piece, in which powder inhaler the chamber is an air compression chamber, the inhaler additionally including a movable obturator designed to be able to close off the orifice, and means for distancing the obturator from the orifice, these means being controlled by the detector.

The delivery of the compressed air is controlled by the displacement of the obturator. The freeing of the orifice permits instant delivery of the air in such a way that all the powder is administered during the aspiration. The mechanism for synchronized control of the obturator has a simple structure and is small in size.

BRIEF DESCRIPTION OF THE DRAWING

Other characteristics and advantages of the invention will be further evident from the following description of an embodiment which is given by way of nonlimiting example. In the attached figures.

DETAILED DESCRIPTION OF A PREFERRED EMBODIMENT

Figure 1:
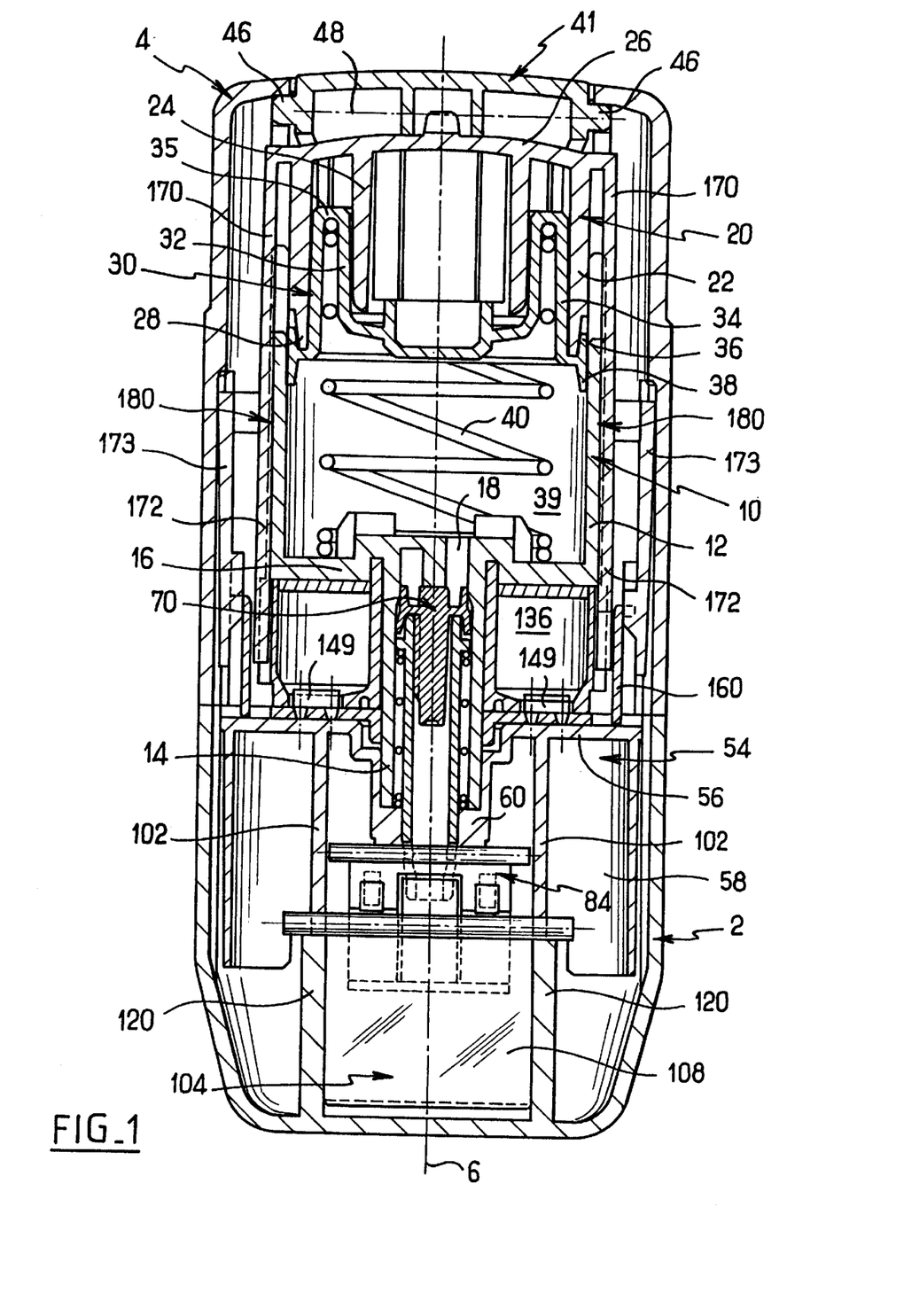
FIG. 1 is an axial cross-section, from the front, of an inhaler according to the invention in the rest position.
Figure 2:
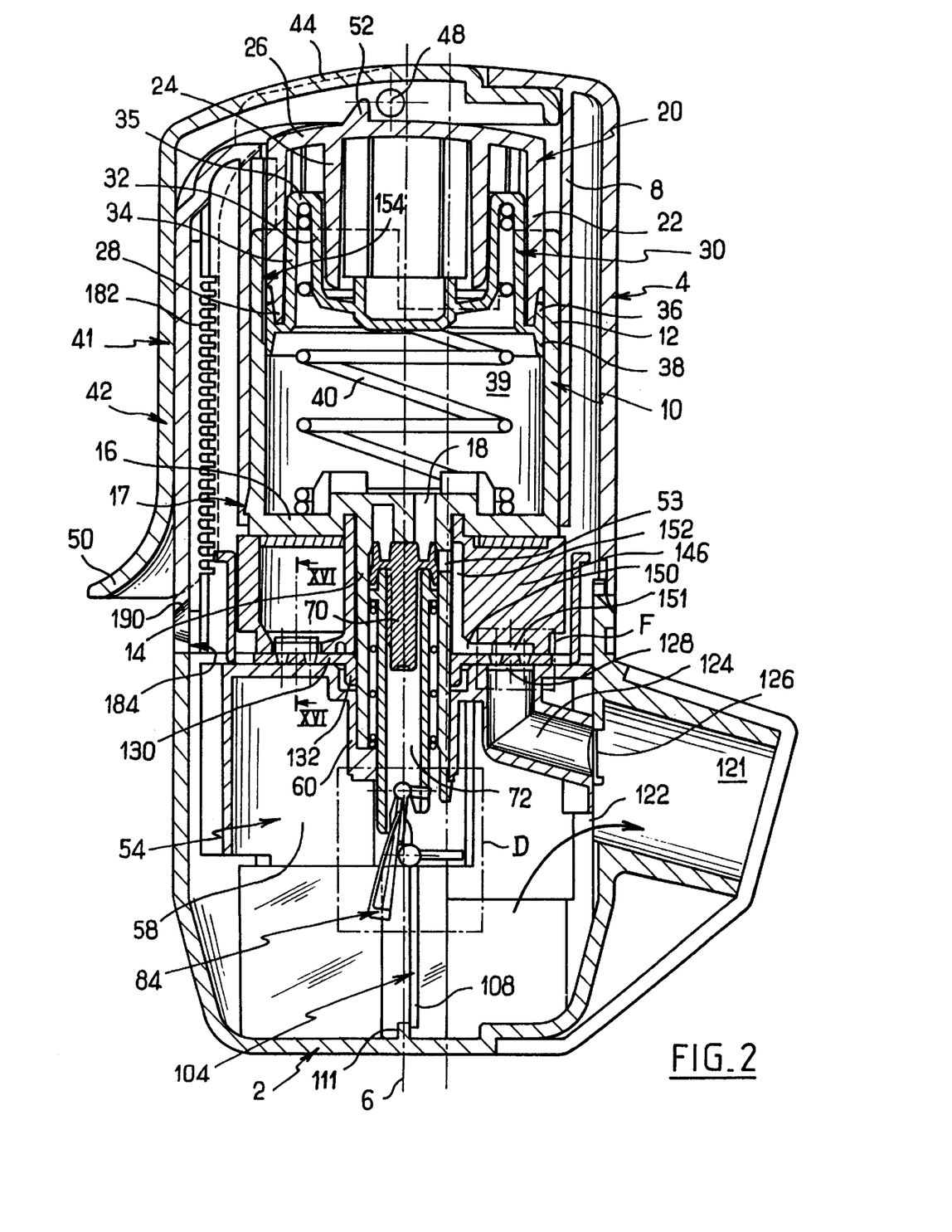
FIG. 2 is an axial cross-section, from the left, of the inhaler in FIG. 1.

With reference to FIGS. 1 and 2, the portable inhaler for administration of medicinal powder includes a casing comprising a lower half casing 2 and an upper half casing 4, both including an external wall of general cylindrical shape with common axis 6. The two half casings are in mutual contact along a joining plane perpendicular to this axis. The upper half casing 4 includes a cylindrical internal skirt 8 of axis 6 which is made integral with the external wall via ribs extending along the entire height of the skirt. These ribs strengthen the upper half casing 4.

The inhaler also includes an internal support 10 comprising a cylindrical body 12, a cylindrical hub 14, both of them hollow and with axis 6, and a bottom 16 perpendicular to this axis and connecting one end of the body to one end of the hub. The interior of the hub communicates with the interior of the body by way of a passage 18 formed in the bottom 16.

With reference to FIG. 2, the external face of the cylindrical body has three studs 17 projecting from this face and distributed around the axis 6 in the vicinity of the bottom 16. The internal skirt of the upper half centre has cavities with a hollow shape corresponding to the relief shape of the studs for the purpose of receiving these. The support is fixed to the upper half casing by engaging the body 10 therein. The studs and the cavities constitute clipping means for securing the support to the half casing, immobilizing these in terms of translation along the axis 6 and in terms of rotation about this axis.

The inhaler includes a piston holder 20 comprising an external wall 22 and an internal skirt 24, both cylindrical and with axis 6. It also comprises an upper end wall 26 of generally plane shape, slightly convex and bulging outwards, extending transverse to the axis 6, and to which upper end wall 26 the external wall and the skirt are fixed. The piston holder is mounted slidably along the axis 6 on the body 12 of the support, the internal face of the body guiding the external face of the external wall of the piston holder. The external wall 22 of the piston holder has an edge 28 opposite the convex wall 26. This edge has a thickness (transverse to the axis 6) which is reduced compared to the thickness of the rest of the external wall. The edge extends in continuity with the internal face of this wall, and set back from the external face of this wall. This edge thus extends at a distance from the internal face of the body 12.

Moreover, the inhaler includes an upper piston 30 comprising an internal skirt 32 and an external skirt 34, both of a general cylindrical shape and with axis 6. The piston is inserted partially into the piston holder 20 between the external wall 22 and the skirt 24. The external skirt 34 of the piston is in contact with the external wall 22 of the piston holder, and the internal skirt 32 of the piston is in contact with the skirt 24 of the piston holder. The two skirts of the piston are connected to each other in an airtight manner via an annular bottom 35 extending at one end of the piston adjacent to the convex wall 26 of the piston holder. The two skirts of the piston are clamped between the wall and the skirt of the piston holder in order to secure the piston to the piston holder. The external skirt of the piston includes, at one end adjacent to the edge 28, an annular continuation comprising two lips 36, 38 of truncated shape and oriented in opposite directions from one another. The two lips are in contact with the internal face of the body 12 in order to ensure airtight contact between the piston and the body. The piston and the support thus delimit an air compression chamber 39. The edge 28 of the piston holder is clamped between the lip 36 and the external skirt of the piston. The inhaler also includes a return spring 40, with axis 6, having a first end bearing on the bottom 16 of the support, and a second end bearing on the bottom 35 of the piston between the two skirts of the piston. This spring tends to distance the piston from the bottom 16.

Figures 3, 4, 5:
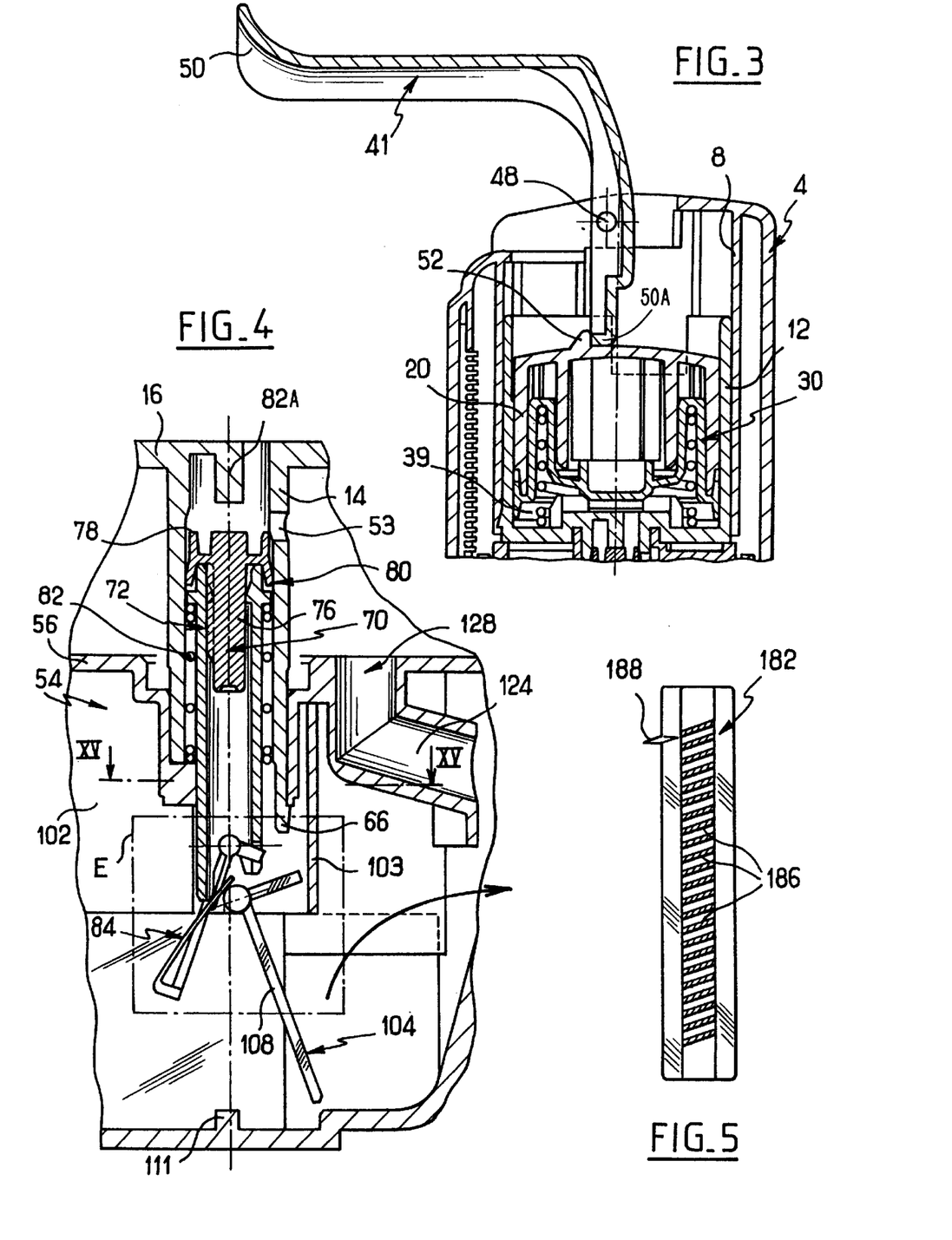
FIG. 3 is a partial view, similar to FIG. 2, showing the lever in the raised position.
FIG. 4 is a partial view, on an enlarged scale, similar to FIG. 2, showing the flap mechanism when inspiration is created in the mouthpiece.
FIG. 5 is a front view of the rack.

With reference to FIGS. 2 and 3, the inhaler additionally includes a lever 41 comprising two portions 42, 44, each having a general rectilinear elongate shape and being arranged perpendicular to one another, forming an approximately 90° bend. When the lever is in the rest position, as represented in FIG. 2, the first portion 42 extends parallel to the axis 6 against the outer wall of the upper half casing, and the second portion 44 extends in a direction generally perpendicular to the axis 6 and bearing on the convex wall 26 of the piston holder. The lever includes two journals 46 coaxial with each other, and the outer wall of the upper half casing has orifices in which the journals are engaged, in such a way as to render the lever mobile in rotation relative to the upper half casing along an axis 48 perpendicular to the axis 6 extending from left to right and offset towards the rear in relation to the axis 6. The journals extend to a middle area of the second portion 44. The first portion 42 has a curved end 50 extending in the direction away from the casing when the lever is in the rest position. This end makes it easier to grip the lever. When the user takes hold of the first portion 42 and drives the lever in rotation in the clockwise direction in FIG. 2, an end 50A of the second portion opposite the bend comes to bear on the convex wall 26 of the piston holder. This wall acts as a ramp for this end 50A upon rotation of the lever, transforming the rotational movement of the lever into a sliding movement of the piston/piston holder assembly in the direction of the bottom 16. The actuation of the lever thus compresses the air held in the chamber 39. The convex wall 26 of the piston holder has, on its external face, a relief 52 arranged in such a way that the end 50A of the lever comes into abutment against this relief when the second portion 44 extends parallel to the axis 6, thereby defining the end of the travel of the lever. In this position, the piston, stressed in the direction of the lever by the compressed air and the spring 39, stresses the lever in a direction intersecting the axis 48. The piston cannot then actuate the lever in order to rotate it. The lever and the relief thus constitute means of locking the piston in the compression position of the chamber, namely means for locking the chamber in a compression state. The user does not therefore take any action in order to maintain this chamber in a compression state.

With reference to FIG. 4, the hub 14 has a first portion adjacent to the bottom 16 and of internal radius r1, and a second portion forming a continuation of the first portion, remote from the bottom 16 and of internal radius r2 slightly greater than r1. The wall of the hub has a lateral orifice 53 extending perpendicular to the axis 6 and situated at the junction between the two portions.

With reference to FIGS. 1, 2, 14 and 15, the inhaler includes a base 54 comprising a plane upper plate 56 oriented perpendicular to the axis 6, and a noncontinuous lateral wall 58 consisting of a rear part, in the general shape of a semi-cylinder with axis 6, and a front part as a cylinder sector with axis 6. The base also comprises a central shaft 60 having the general outer shape of a cylinder with axis 6, extending from the plate 56, on the same side thereof as the noncontinuous wall 58. One end of the shaft remote from the plate 56 has three first internal cylindrical bearing spans 62 of axis 6 and radius r3, which will be referred to hereinafter as hub spans, and three second internal cylindrical bearing spans 64, of axis 6 and radius r4 smaller than r3, which will be referred to hereinafter as obturator spans. The hub spans 62 are offset angularly about the axis 6 in relation to the obturator spans 64 with which they alternate about the axis 6. The junction between the first and second adjacent spans is provided by a noncontinuous shoulder 65 at the end of the shaft. Between the plate 56 and this shoulder, the shaft has a cylindrical internal face of axis 6 and radius r3. This radius r3 is equal to the external radius of the hub 14. The base 54 is mounted on the support 10, the shaft 60 being engaged on the hub 14. The internal face of the shaft is in surface-to-surface contact with the external face of the hub. The end of the hub 14 remote from the bottom 16 includes three studs 66 extending transversely outwards from the external face of the hub, and arranged to extend outside the shaft, bearing axially at the end thereof. These studs constitute means of clipping the base 54 on the hub in order to secure the base and the hub 14. The base is fixed relative to the casing.

With reference in particular to FIGS. 4, 6, 7 and 8, the inhaler includes an obturator 68 comprising a lower piston 70 made of elastomer and a lower piston holder 72. The lower piston holder 72 has a general cylindrical shape of axis 6. It has a cylindrical external face of radius r4 in surface-to-surface contact with the obturator spans 64. The lower piston holder extends within the channel defined by the interior of the hub and communicating with the chamber. Near one end adjacent to the bottom 16, it has an external flange of radius r2 in contact with the internal face of the hub. The internal Lace of the hub and the spans 64 of the base provide for the slidable guiding of the lower piston holder 72, and thus of the obturator, in the hub along the axis 6.

The lower piston 70 includes a cylindrical central core 76, of axis 6, the greater part of which is engaged in the lower piston holder. The core has external ribs, and the piston holder includes internal stops cooperating with the ribs in order to prohibit the escape of the core from the piston holder. The piston is thus secured to the lower piston holder. The lower piston includes an annular flange extending transversely in projection from the core and bearing on the end of the piston holder adjacent to the core and near the bottom 16. This flange has two lips, upper lip 78 and lower lip 80, which are of truncated shape and are oriented in opposite directions from one another. The upper lip 78 is adapted to ensure, where appropriate, a leaktight connection between the piston 70 and the hub portion of internal radius r1, and the lower lip 80 is adapted to ensure, where appropriate, a leaktight connection between the piston and the hub portion of internal radius r2. The support 10 includes a continuation 82A extending within the passage 18 along the axis 6, constituting a stop for the end of the core 76 adjacent to the flange. This continuation is arranged in such a way that when the obturator is in abutment on this continuation, the orifice 53 of the hub is situated between the two lips 78, 80. The upper lip 78 then provides for the leaktightness of the connection between the piston and the hub. The air compression chamber 39 is thereby closed, and the end face of the lower piston adjacent to the upper lip 78 is subjected to the pressure prevailing in the chamber 39. When this pressure is greater than the atmospheric pressure, the obturator 68 is thus stressed along the axis 6 in the direction distancing it from the bottom 16 of the support, namely towards the bottom in the figures. The inhaler includes a return spring 82 having a first end bearing on the shoulder 65 of the shaft and a second end bearing against the flange of the lower piston holder. This spring stresses the obturator along the axis 6 in the direction moving it towards the bottom 16 of the support, i.e. towards the top in the figures.

Figure 6:
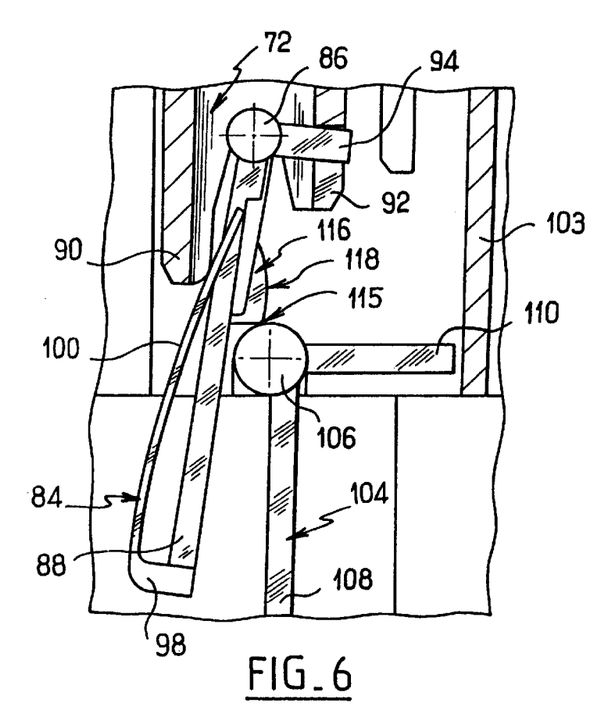
FIG. 6 is a view, on an enlarged scale, of the detail D from FIG. 2.
Figure 7:
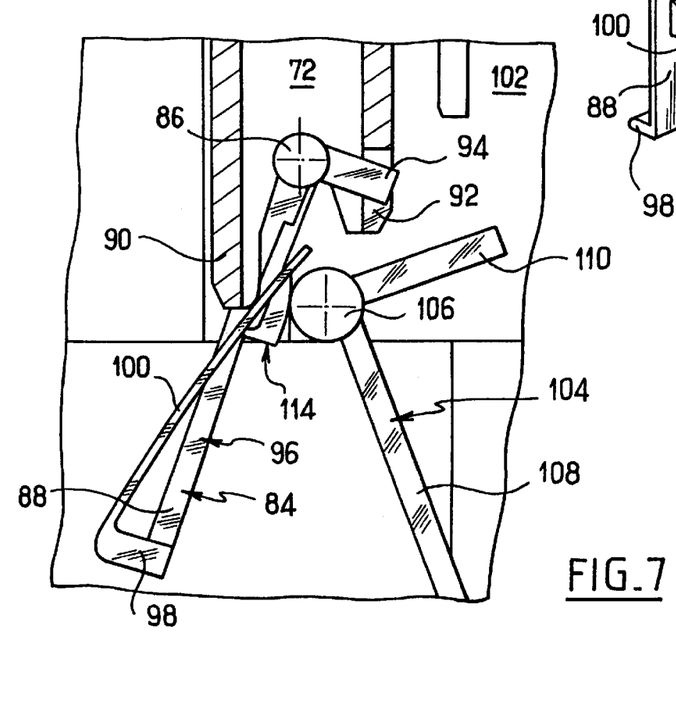
FIG. 7 is a view, on an enlarged scale, of the detail E from FIG. 4.
Figure 8:
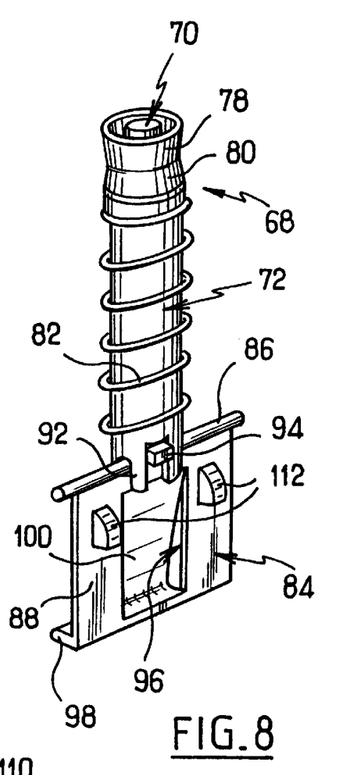
FIG. 8 is a perspective view of the obturator and of the ratchet.

With reference to FIGS. 1, 2, 4, 6, 7 and 8, the inhaler includes an immobilizer in the form of a ratchet 84 comprising a journal 86 and a wall 88 of general rectangular shape which is fixed via one edge to the journal. The lower piston holder 72 is cut out at an end opposite the piston 70 in such a way as to define a wide rear tab 90 and two narrow front tabs 92 close to one another. The cutout between the rear tab 90 and each of the two front tabs 92 is shaped as an arc of a circle, in such a way that the journal 86 is clipped between the rear tab and the two front tabs. The journal 86 extends perpendicular to the axis 6, from left to right, intersecting this axis. The clipping renders the ratchet 84 movable in rotation by a small extent in relation to the lower piston holder 72 about the axis of the journal. The ratchet 84 includes a catch 94 fixed to the journal and extending transverse to the axis 6, perpendicular to the wall 88 on the side of the front tabs 92 and between these. This catch is designed to bear against the wall of the lower piston holder 72 at the junction between the two front tabs 92 when the ratchet is arranged with its wall 88 substantially parallel to the axis 6, as is represented in FIG. 6, with the ratchet in the rest position.

The wall 88 of the ratchet has at its centre a rectangular recess 96 extending substantially from the journal to the lower edge of the wall opposite the journal. At this edge, the wall has a rectilinear flange 98 extending along the entire length of this edge, on that side of the wall opposite the catch 94. The ratchet includes a flexible plane blade 100 extending, before assembly, from this flange 98 parallel to the wall 88. The blade has a rectangular shape close to that of the recess 96. The blade extends in line with this recess. Its dimensions are adapted to permit an upper part of the blade to pass through the recess under the effect of stressing. The blade 100 and the rear tab 90 of the lower piston holder are arranged in such a way that the rear tab stresses the blade permanently and provokes its flexion. The blade thus at all times partially passes through the recess. In the rest position of the ratchet, as represented in FIG. 6, with the wall 88 substantially parallel to the axis 6, the rear tab stresses the blade minimally. The stressing is more intense, and thus the flexion of the blade is more pronounced, when the ratchet is tilted rearwards, namely in the clockwise direction as in FIG. 7.

The base 54 includes two plane walls 102 parallel to each other and extending from the plate 56 in line with the shaft parallel to the axis 6, and being oriented from front to rear. The base also includes a plane rectangular panel 103 extending from one wall 102 to the other perpendicularly thereto and parallel to the axis 6, in front of the shaft 60, and being oriented from left to right.

The inhaler includes a flap 104 comprising a journal 106 and a panel 108 of a general rectangular shape which is fixed via one edge to the journal. The ends of the journal are clipped into cutouts of circular arc shape in the lower edge of the two walls 102. The journal 106 extends parallel to the journal 86 of the ratchet, in the continuation of the lower piston holder 72, and slightly offset towards the front in relation to the journal 86 of the ratchet, namely in the direction of the front tabs 92. The journal 106 extends in the continuation of the obturator. The flap 104 is movable in rotation, in relation to the base, about the axis of the journal 106. The panel 108 is fixed to the journal 106, being offset laterally towards the front in relation to the axis of the journal. The flap includes a plane rectangular cap 110 which is fixed via one edge to the journal and is arranged perpendicular to the panel 108 towards the front. The cap is disposed in such a way that when the flap is at rest, with the panel 108 substantially parallel to the axis 6, the cap extends between the walls 102 and the panel 103 of the base, roughly closing off the space delimited by these on the side opposite the panel 108 of the flap. Total closure is not necessary. The lower half casing includes a stop 111 for the panel 108, limiting the rearward rotation of the flap and defining the rest position of the flap with the vertical wall 108.

The wall 88 of the ratchet has, on its front face, two studs 112 arranged on either side of the recess 96 in proximity to the journal 86. Each stud 112 has a plane lower face 114 perpendicular to the wall 88 and parallel to the journal 86, two plane lateral faces 116 parallel to each other and perpendicular to the wall 88 and to the journal, and a convex curved face 118 extending from the wall 88 to the lower face 114, forming a sharp edge 115 at approximately 90° thereto. The studs are arranged in such a way that when the obturator 68 is in abutment on the continuation 82, the studs rest via their sharp edge on the journal 106 of the flap, as is shown in FIG. 6. The sharp edge of the studs is situated in proximity to the summit of the journal, being slightly offset towards the rear in the direction of the wall 88 of the ratchet. This position is defined by the catch 94 abutting against the lower piston holder and is held by the cooperation of the rear tab 90 and the blade 100 as long as the flap remains in the rest position.

The lower half casing includes two plane deflectors 120 which are parallel to each other and extend vertically, parallel to the axis 6, from the lower face of the half casing in the direction of the base 54. The deflectors 120 extend in the continuation of the two walls 102 of the base, in respective continuity with these, as is shown in FIG. 1. An upper edge of each deflector is in contact with the lower edge of the associated wall 102 in a substantially airtight manner. The distance between the two deflectors 120 is very slightly greater than the length of the panel 108 of the flap parallel to the journal 106, so that the flap 104 is free to turn about its axis of rotation, with a certain degree of airtightness being ensured between the flap and the deflectors.

With reference to FIGS. 2 and 4, the lower half casing 2 includes, on its front face, an inhalation mouthpiece 121 for a patient, bringing the interior of the inhaler into communication with the outside. The mouthpiece extends in a direction generally perpendicular to the axis 6, and is oriented slightly downwards. The front part of the lateral wall 58 of the base extends in line with this mouthpiece. Its dimension along the axis 6 is sufficiently reduced to form a space 122 for communication between the mouthpiece 121, on the one hand, and the base 54 of the lower half casing 2, on the other, as far as the flap on the front face of the panel 108. The rear part of the lateral wall 58 of the base extends at a distance from the rear lateral wall of the lower half casing. The space thus formed is in communication with the space delimited between the wall of the upper half casing 4 and the skirt 8, this space communicating with the outside via the summit of the upper half casing. The rear face of the panel 108 of the flap is thus also in communication with the outside.

The base includes a channel 124 comprising two portions extending in a continuation of one another and forming a bend. The first portion extends immediately upstream of the mouthpiece, parallel to the latter, in such a way as to lead into the mouthpiece. The free end of this portion has a grille 126 for fractionation of the powder to be administered to the patient. The grille extends transverse to the axis of the portion. The second portion is fixed to the upper plate 56 of the base, in line with a circular orifice 128 thereof into which it leads. The second portion is substantially parallel to the axis 6, namely vertical in this case.

With reference to FIGS. 1, 2, 11 and 12, the inhaler includes a plate 129 for transferring and metering the powder. This plate comprises a circular disc 130, of axis 6, having a central orifice, the disc being continued axially downwards at the level of the orifice by a ring 132. The plate is engaged, via this central orifice, on the hub 14, in surface-to-surface contact with the latter. The lower face of the disc extends on the plate 56 of the base. Formed in the disc there are cells 134 which pass through the thickness of the disc along the axis 6. These cells are distributed in ten groups of six cells. The cells of each group are arranged in a circle. The volume of each group of cells corresponds to one dose of powder to be administered. The orifice 128 of the base has a diameter which is sufficient to envelop the diameters of the cells of a same group. The groups are arranged in a circle, centred on the axis 6. The cells have a truncated profile parallel to the axis 6, the narrow section of the cone being situated on the side towards the plate 56 of the base, namely on the downstream side of the cells in relation to the direction of flow of the compressed air, as will be seen. The cells thus have a cross-section which decreases downstream.

Figures 11, 12, 13:
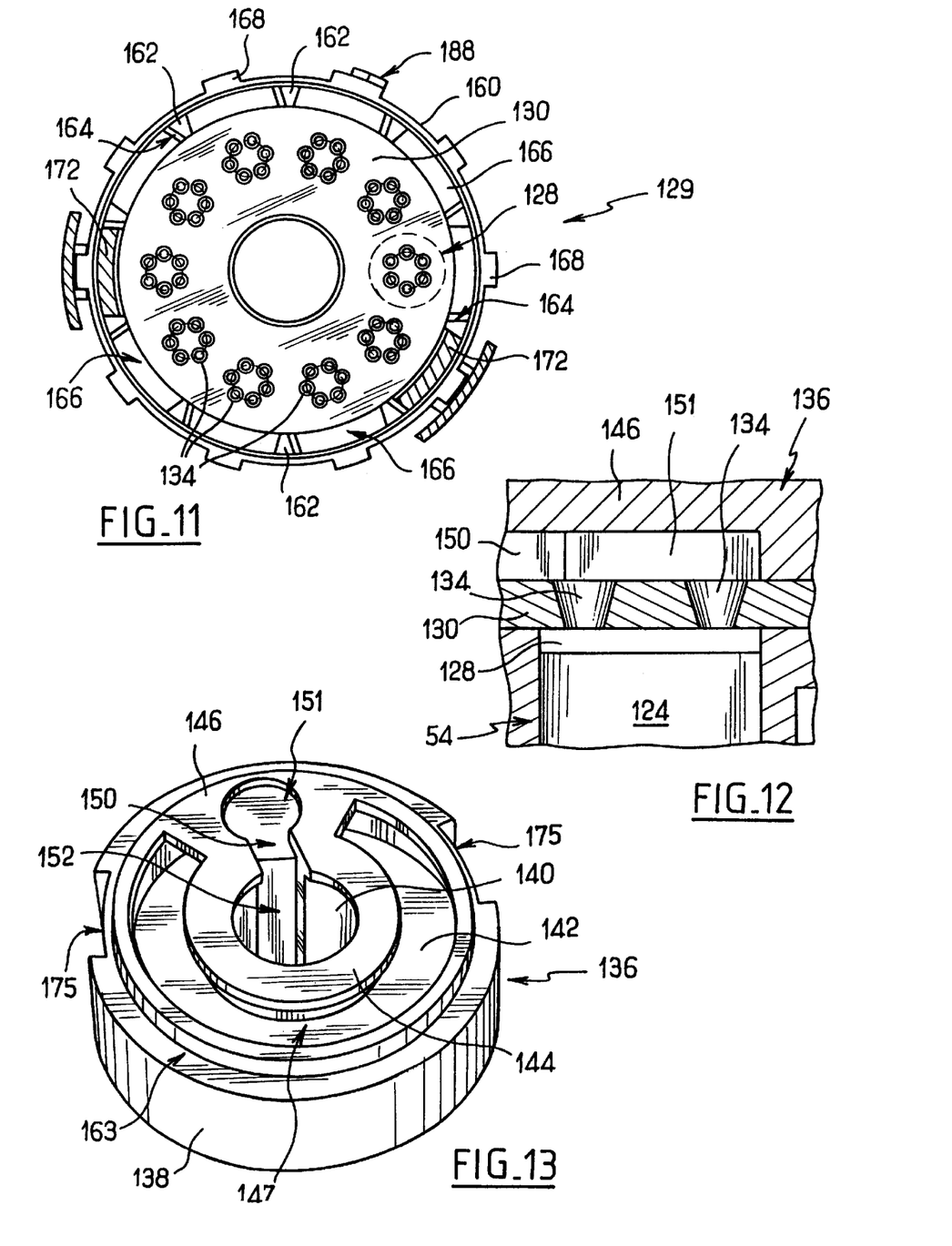
FIG. 11 is a transverse cross-section along the plane XI—XI in FIG. 10.
FIG. 12 is a view, on an enlarged scale, of the detail F from FIG. 2.
FIG. 13 is a perspective view of the powder magazine.
Figures 14, 15, 16:
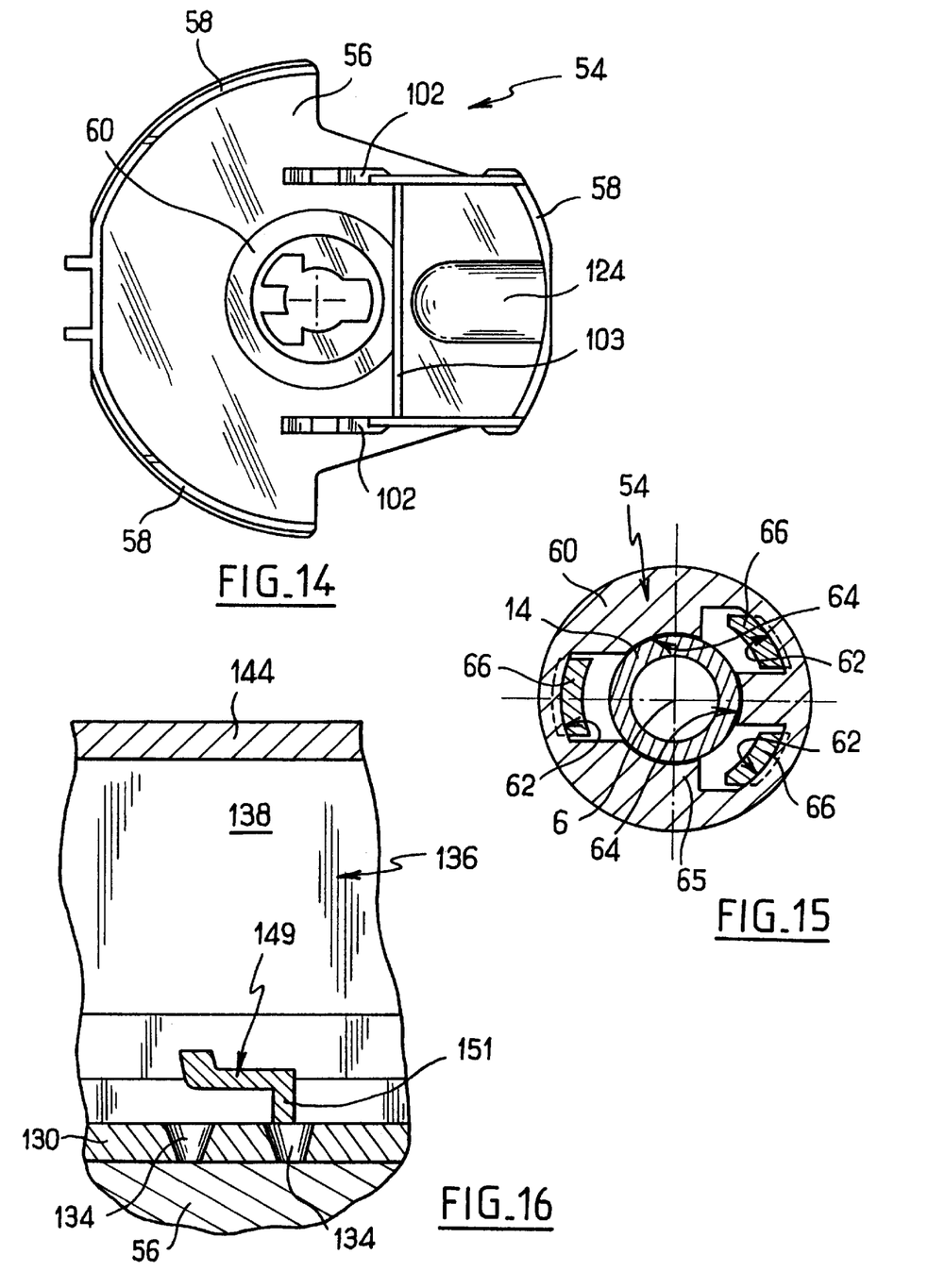
FIG. 14 is a bottom view of the base.
FIG. 15 is a cross-section along the plane XV—XV in FIG. 4.
FIG. 16 is a cross-section along the plane XVI—XVI in FIG. 2.

With reference to FIGS. 1, 2 and 13, the inhaler also includes a magazine 136 of powder intended to be administered to the patient. This magazine comprises a peripheral cylindrical wall 138 and a central cylindrical wall 140, both of axis 6. It comprises two circular walls, upper 142 and lower 144. For the sake of clarity, the magazine has been turned around in FIG. 13 so that the position of the circular walls is inverted. The central cylindrical wall 140 is in contact with the hub 14 on which the magazine is engaged, slightly clamped between the wall and the hub in order to prevent any intrusion of powder between the wall and the hub and any loss of air when the compressed air is freed, as will be seen. The magazine is immobilized in relation to the hub. The upper face of the upper wall 142 is in contact with the bottom 16 of the support. The lower face of the lower wall 144 is in contact with the disc 130 of the plate. The magazine is generally hollow between its four walls, except over an angular spacing sector 146 above a group of cells, where the magazine is made solid, as is shown in FIGS. 2 and 13. The lower circular wall 144 has a recess 147 in the shape of an arc of a circle interrupted in the area of the solid sector 146. The magazine thus has a generally toric shape and defines an enclosure filled with powder. The upper circular wall 142 is formed by a movable lid fixed to the magazine in a manner leaktight to the powder and allowing the magazine to be filled. The powder in the magazine passes through the recess 147 by gravity and settles in the cells 134 of the plate. The cells are filled with the powder in the direction in which the compressed air passes through the cells, from upstream to downstream. As will be seen, the plate is movable in rotation about the axis 6 in relation to the magazine. The magazine includes scrapers 149 which can be seen in particular in FIG. 16 but which are not shown in FIG. 13. These scrapers include a blade 151 which is generally radial and parallel to the axis 6, passing through the recess 147, and bearing elastically against the upper face of the disc 130 of the plate, and extending in the trajectory of the groups of cells. Upon passage of a scraper, the powder is packed into the cells. The upper plate 56 of the base extends against the lower face of the disc 130 and prohibits the escape of powder from the cells, except in the area of the orifice 128 upon administration of the powder, as will be seen. The disc thus extends between the lower face 144 of the magazine and the plate 56 of the base.

In the area of the solid sector 146 of the magazine, the lower circular wall 144 has a circular recess 151 with the same shape and the same dimensions as the orifice 128 in the base. This recess remains in line with the orifice in the base. It is continued in the direction of the axis 6 by a short groove 150. The central cylindrical wall 140 has a second groove 152 of rectangular profile in the direction transverse to the axis 6. This groove 152 extends parallel to the axis 6, from the groove 150, with which it communicates, to a point in line with the orifice 53 of the hub, being interrupted before the upper circular wall 142 of the magazine.

The functioning of the inhaler will now be explained with regard to the elements which have been described up to now.

At rest, the inhaler is situated in the position represented in FIGS. 1, 2 and 6. The lever 41 bears against the upper half casing 4. The upper piston 30 is stressed upwards by the spring 40 and is in the upper position in abutment against the lever. The interior of the compression chamber 39 is at atmospheric pressure. The obturator 68 is stressed upwards by the spring 82 and is in the upper position, abutting against the continuation 82A. The upper lip 78 of the lower piston is applied in an airtight manner against the upper portion, of small internal radius r1, of the hub. The obturator thus closes off the orifice 53 of the compression chamber 39. The blade 100 of the ratchet is stressed forwards by the rear tab 90. The catch 94 is in abutment against the lower piston holder. The sharp edge 115 of the studs is in contact with the journal 106 of the flap. The flap extends with its panel 108 parallel to the axis 6 under the effect of gravity.

To administer a dose of powder, the patient pivots the lever in the clockwise direction as far as the position represented in FIG. 3. This pivoting causes the upper piston holder 26 and the upper piston 30 to slide as far as their lower position close to the bottom 16. This sliding generates an increase in the air pressure in the chamber 39. This is because the ratchet 84 bearing on the flap 104 cannot slide downwards. The obturator 68 is thus also immobilized. When the upper piston 30 reaches the end of its travel in the lower position, the air in the chamber 39 is compressed to the maximum pressure. This pressure stresses the upper face of the obturator downwards in the direction of the flap. This stressing translates into the studs 112 bearing on the flap via their sharp edge 115 while remaining immobilized, which prohibits the sliding of the obturator. The lever in the raised position locks the upper piston 30 in the lower position. The inhaler is thus loaded and remains so, without any action on the part of the patient, until the patient triggers the administration of the treatment. As will be seen hereinafter, a group of cells is situated at this moment in line with the orifice 128 of the base. The packing of the powder in the cells and the shape of the cells prevent the powder from escaping naturally from the cells and through the plate, for example by gravity. It will be noted that the flap mechanism is loaded by the pressure of the compressed air in the chamber, without any other means such as a loading spring.

The patient places his mouth round the mouth-piece 121 in such a way as to be able to breathe in through the mouthpiece. The patient breathes in. This breathing-in creates an underpressure on the front face of the flap 104. The flap is rotated forwards, in the anti-clockwise direction in FIGS. 4 and 7. The start of the rotation of the journal 106 of the flap causes the escape of the sharp edge 115 of the studs and the cessation of the bearing. Under the influence of the obturator subjected to the pressure in the now released chamber, the ratchet is driven in rotation about its journal 86, rearwards in the clockwise direction, whilst the obturator slides along the axis 6 in the direction of the flap. The ratchet, stressed via the blade 100 by the rear tab 90 of the hub, is placed bearing against the journal 106 of the flap via the curved faces 118 of the studs. As soon as the obturator starts to slide, the lower lip 80 of the lower piston comes into airtight contact with the second portion, of large internal radius r2, of the hub. Moreover, the leaktight contact between the upper lip 78 of the lower piston and the hub is interrupted. The obturator is situated at a distance from the orifice. The compressed air from the chamber 39 escapes through the orifice 53 of the hub, follows the groove 152, then the groove 150 of the magazine outside the hub, then ends up in the recess 151. Here, it forces the powder from the group of cells arranged in the area of the recess to pass through the disc 130 and it entrains this powder into the channel 124 of the base. The powder is fragmented by the flow of air, then by passing through the grille 126 downstream of the plate. The air carrying the powder passes through the mouthpiece 121 and finally reaches the user's lungs. The release of the compressed air is thus triggered by the patient breathing in. The flow of the freed compressed air passes vertically downwards through the cells. The flow of compressed air is thus added to the weight of the powder in order to transport this powder and fragment it.

As soon as the patient stops breathing in, the flap 104 pivots rearwards by gravity so as to return to its rest position. The spring 82 of the obturator is designed in such a way that it returns the obturator upwards in the direction of the bottom 16 as soon as a pressure close to atmospheric pressure prevails in the compression chamber following escape of the compressed air. The upward sliding of the obturator until it comes into abutment against the continuation 82 results in the closure of the orifice 53. At the end of this sliding, the rear tab 90 of the hub, stressing the blade 100, pushes the ratchet so as to bring the studs 112 into contact via their sharp edge with the journal of the flap, as before.

When the patient once again lowers the lever into the rest position, the return spring 40 returns the upper piston 30 to its upper rest position. The inhaler is now ready for use again. The spring 40 has a tension which is sufficiently low to allow the patient to load the inhaler without effort. Consequently, it may happen that this spring will develop a force of reaction which is of insufficient intensity to push the piston over the last ⅙th of its travel to the upper position, on account of the underpressure then arising in the newly closed off chamber 39. This is why it is advantageous to form, in the internal face of the body 12 of the support, a duct 154 extending parallel to the axis 6 from the free upper end of the body along a length sufficient to interrupt the leaktight contact of the lips 36, 38 of the upper piston with this internal face after the piston has travelled ⅚ths of its course. On the last ⅙th of the course, the outer air is introduced via the duct 154 into the chamber 39, and this eliminates the underpressure. The spring can then push the piston to its upper position.

It will be seen that the inhaler includes a first conduit defined by the grooves 152 and 150, the channel 124 and the mouthpiece 121, and passing through the orifice 128. This conduit is intended for the passage of the compressed air escaping from the chamber, the dose of powder to be administered being dispersed in this conduit. It will also be seen that the inhaler includes a second conduit delimited between the upper half casing 4 and the skirt 8, the lower half casing 2 and the base 54 and the mouthpiece 121, and passing through the space 122. This conduit is distinct from the first one. The flap and the ratchet extend within this conduit. The flap extends outside the trajectory of the powder and does not risk impeding its entrainment by the flow of air. The mechanism formed by the ratchet and the flap does not risk being damaged by deposits of powder.

The abovementioned fit between the flap and the walls 120 means that a slight aspiration on the part of the patient provokes the displacement of the flap. The sensitivity of the triggering of the flap depends on the quality of the fit.

The flap and the ratchet constitute means of controlling the distancing of the obturator 68 from the orifice 53 with a view to terminating its closure and freeing it for the escape of the compressed air from the chamber 39. This means is designed to be actuated by a suction created in the mouthpiece 121. The flap mechanism, including three components which are movable in relation to one another (the flap, the ratchet and the obturator), is of a relatively simple structure.

Figures 9, 10:
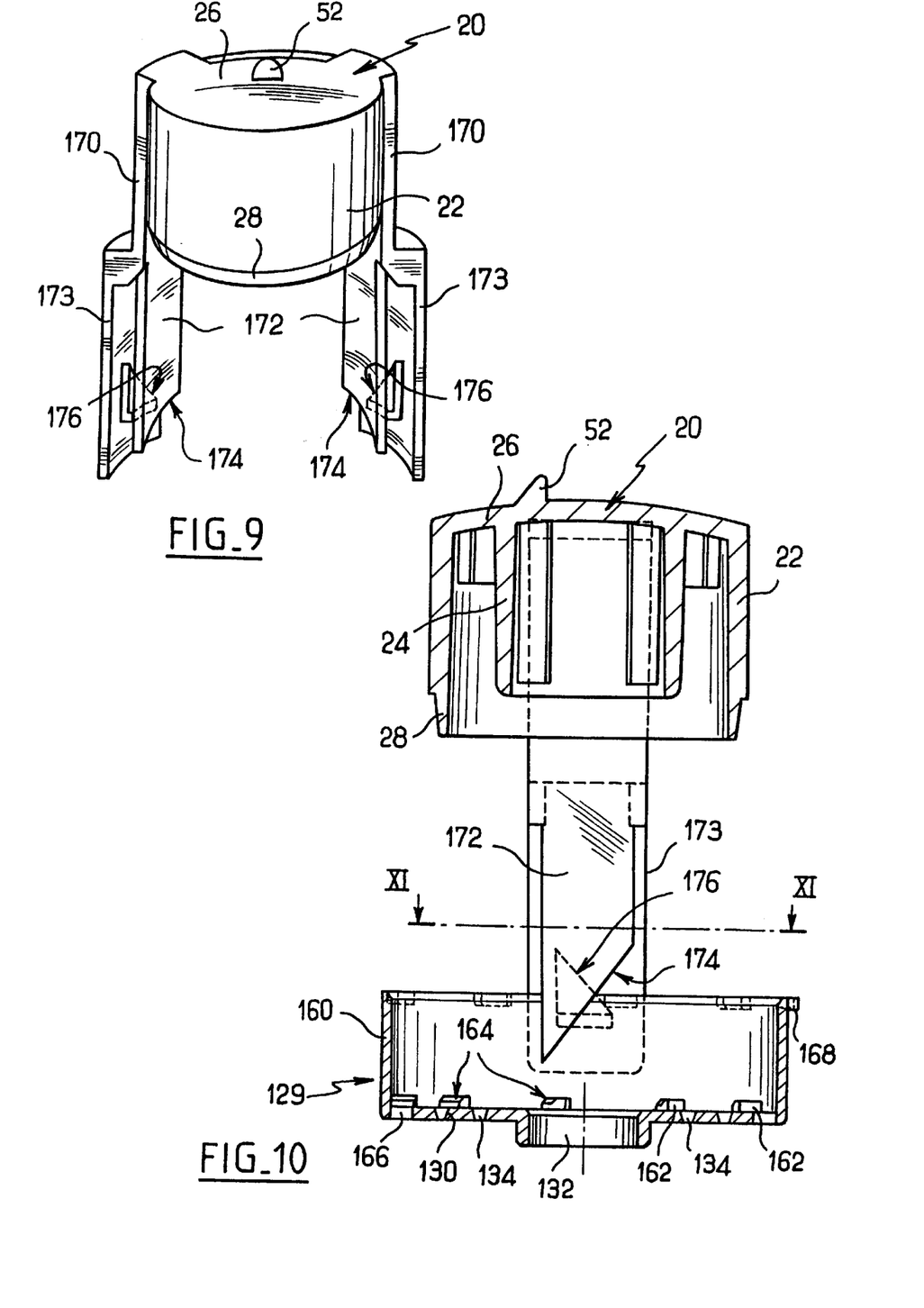
FIG. 9 is a perspective view of the piston holder.
FIG. 10 is an axial cross-section through the piston holder and the plate.

With reference to FIGS. 1, 10 and 11, the plate includes a cylindrical lateral wall 160, of axis 6, extending about the perimeter of the disc 130, upwards from one side of the disc facing the peripheral wall 138 of the magazine. The disc has ten bosses 162 uniformly distributed about the perimeter of the disc, being contiguous internally with the wall 160. These bosses project from the upper face of the disc, opposite the magazine. The latter has a shoulder 163 at the junction between the peripheral wall 138 and the lower wall 144. This shoulder constitutes a seat for the bosses. The bosses are profiled in the radial direction to the axis 6. They have a rectangular profile, an upper edge of the rectangle being chamfered to define a bevel face 164 inclined upwards and in the direction of the succeeding boss of the series. The disc has recesses 166 in the shape of circular arcs which are formed between the successive bosses. The lateral wall 160 of the plate has, at its upper edge, ten tongues 168 of rectangular shape which project radially from the external face of the wall. The tongues are situated at the level of the respective recesses 166, in plan view.

With reference to FIGS. 1, 9 and 10, the upper piston holder includes two lateral continuations 170 extending from the upper wall 26 and in line with the lateral wall 22, parallel to the axis 6. The two continuations form, with the axis 6, an angle of approximately 150 degrees. At one end extending beyond the lower edge 28 of the lateral wall 22, each continuation divides into two elongate arms 172, 173 of cylindrical shape, with axis 6, concentric to each other and arranged facing each other, extending along the axis 6.

The first arm 172 continues in the line of the extension 170. It has a lower chamfered end defining a bevel face 174 inclined downwards and laterally. The two bevel faces 174 of the arms 172 are oriented in opposite directions. The arms 172 extend opposite the internal face of the lateral wall 160 of the plate. The width of an upper part of the first arm is identical to that of the associated continuation, and the width of a lower part of the first arm is very slightly smaller than the length of the recesses 166 of the disc. The arm is dimensioned to be able to engage in these recesses, as is shown in FIG. 11. The peripheral wall 138 of the magazine 136 has two notches 175 extending along the axis 6, having the same width and the same thickness as the first arms 172, and arranged to form an identical angle with the axis 6. The arms 172 are housed in these notches which allow the arms to slide relative to the magazine parallel to the axis 6.

The second arm 173 of each continuation is offset outwards relative to the axis 6 and extends opposite the external face of the lateral wall 160 of the plate. It has, on its internal face, a relief which has, in elevation, the general shape of a right-angled triangle. The hypotenuse of the triangle constitutes a bevel face 176 inclined upwards and laterally, on the same side as the bevel face 174 of the associated first arm. The bevel faces 176 of the second arms 173 are oriented in opposite directions. The relief is situated opposite the chamfered point of the associated first arm 172. The width of the relief is smaller than the distance separating two tongues 168 of the plate, so that the relief can pass through the space separating two consecutive tongues 168.

With reference to FIG. 1, the body 10 of the support has two grooves 180 extending on the external face of the lateral wall 12 parallel to the axis 6 from the open upper end of the body to the bottom 16. The grooves 180 form, with the axis 6, an angle identical to that of the continuations 170. The width of each groove 180 is equal to the width of the continuation 170 and of the upper part of the first arm 172 which continues it, in such a way that each continuation 170 and its arm 172 are housed partially along their thickness in the corresponding groove 180. The grooves 180 thus participate in the slidable guiding of the upper piston holder 20 relative to the support 10 parallel to the axis 6. Moreover, these grooves prohibit the rotation of the upper piston holder relative to the support about the axis 6. The sliding of the first arms 173 in the notches 175 prohibits the rotation of the magazine 136 relative to the upper piston holder 20 about the axis 6, and consequently relative to the support 10.

The end of the arms 172 is arranged in such a way that, with the inhaler in the rest position, namely when the piston is in the upper position, the bevel face 174 extends above the bosses 162, the bottom portion of the bevel face 174 being situated vertical to the bevel face 164 of one of the bosses, the bevel face of the boss being situated in the trajectory of the bevel face 174. Thus, the downward sliding of the upper piston holder under the action of the lever brings the bevel face 174 of the arm into contact with the bevel face 164 of the boss, these then being oriented parallel to one another. With the bevel face 174 serving as ramp for the bevel face 164 of the boss, the continued sliding of the upper piston holder sets the plate in rotation about the axis 6. When the bevel face 164 of the boss leaves this ramp, the rotation of the plate ceases, and the arm 172 penetrates the respective recesses 166 adjacent to the bevel face 164 of the boss. The plate is then immobilized in rotation relative to the upper piston holder about the axis 6. The upper piston holder and the plate are designed in such a way that this movement of the plate, under the ramp effect, places a group of cells opposite the orifice 128 of the base.

The end of the downward travel of the upper piston holder corresponds to the compression state of the chamber 39. The relief on the arm 173 is arranged in such a way that the bevel face 176 of this arm then extends below the tongues 168. The top portion of the bevel face 176 is situated vertical with an edge of one of the tongues 168, the tongue being in the trajectory of the bevel face. When the patient lowers the lever to the rest position, the upper piston holder slides upwards, which brings the bevel face 176 of the relief into contact with the edge of the tongue 168 opposite. With the bevel face 176 serving as ramp for the edge of the tongue, the continued upward sliding of the upper piston holder sets the plate in rotation about the axis 6, in the same direction as before. During this movement of rotation of the plate, the arm 172 progressively emerges from the recess 166, the rotation being permitted by the pointed shape of the end of the arm 172. The upper piston holder and the plate are designed in such a way that this new movement of rotation of the plate distances the abovementioned group of cells, now empty of powder, from the orifice 128. The rotation of the plate is interrupted when the tongue leaves the bevel face 176. The group of cells then extends between the magazine and the plate 56 of the base. The upper piston holder and the plate are designed in such a way that when the upper piston holder has returned to the rest position in FIG. 1, the bevel face 174 is situated vertical to the next boss 162.

The downward sliding of the upper piston holder thus places a group of cells opposite the orifice 128. Thereafter, the upward sliding of the upper piston holder places this group of cells in a position protected from the orifice 128 and the ambient air. These two movements of the plate are controlled by the actuation of the lever. Thus, the actuation of the lever from the rest position provokes simultaneously the compression of the chamber and the positioning of a group of cells, filled with powder, opposite the orifice 128. The return of the lever to the rest position places this group, emptied of its powder, in a protected position. An advantage of this inhaler is that the cells, whether empty or full, are in contact with the ambient air only at the moment of use of the inhaler, namely when the lever is raised. Their cleanness as regards foreign matter is thus preserved.

With reference to FIGS. 2 and 5, the inhaler includes a rectilinear rule 182 extending parallel to the axis 6. The rear lateral wall of the upper and lower casing halves has, on its internal face, a groove 184 adapted to receive the rule sliding along the axis 6. The rule has, on its face directed towards the axis 6 and opposite the groove, a rack toothing consisting of rectilinear teeth 186 aligned and parallel to each other. The teeth are inclined slightly in relation to the direction transverse to the axis 6. The summit of the teeth has a cylindrical shape of axis 6. One of the tongues 168 of the plate has a counting tooth 188 projecting from a bevel face of the tongue opposite the wall 160. This tooth has a lozenge shape adapted to fit between two successive teeth 186 of the rule during the rotation of the plate. The passage of the counting tooth causes the rule to slide downwards and positions the rule in such a way that, during the next passage, the counting tooth will fit in the space between the following teeth. The rear face of the rule in contact with the groove has a marker (not shown) near its upper end. The upper half casing has a window 190 formed in its rear wall at the bottom of the groove 184 in the trajectory of the marker. The marker and the window are arranged in such a way that the marker is visible from the outside through the window when the counting tooth is engaged in the space between the two uppermost teeth, which corresponds to the end of the downward travel of the rule.

Each use of the inhaler causes the plate to rotate through 1/10th of a turn. At the end of each turn, the counting tooth causes the downward sliding of the rule. Each tooth 186 of the rule thus corresponds to ten uses. The number of teeth is chosen such that the marker appears in the window when the magazine is empty. The rule and the plate constitute a system for counting the number of uses, which system permits a large number of uses to be counted with precision and is of a small size.

The lower and upper casing halves, the upper piston, the upper piston holder, the upper spring, the support, the lower piston, the lower piston holder, the lower spring, the magazine, the plate, the ratchet and the base are all concentric to the axis 6. This characteristic reduces the overall size of the components and reduces the volume of the inhaler. As the inhaler is intended for portable use, this is particularly advantageous.

The inhaler is assembled in the following way. The lower piston and the lower piston holder are joined together. The lower spring is engaged on the latter and the ratchet is clipped onto the lower piston holder. The magazine and the plate are engaged on the hub 14, and the obturator is engaged in the hub. The flap is clipped onto the base 54. The base is engaged on the hub by clipping the base onto the hub, which secures the abovementioned components. The upper spring is placed in the body 10. The upper piston is fixed to the upper piston holder by clamping. The continuations of the upper piston holder are engages in the grooves 180 and the upper piston holder is engaged on the support. The rule is placed in the groove 184 of the upper half casing. The lever is fixed to the upper half casing. The unit comprising the support is placed in one of the casing halves, and the two casing halves are clipped together, these being equipped for this purpose with suitable clipping means.

Assembly of the inhaler is simple and quick, especially because of the presence of the support 10 which is common to a large number of components. This support allows the components concerned to be joined together before they are introduced into the casing. The clipping together of the components also makes this assembly easier.

All the components, with the exception of the springs, the grille and the lower piston, can be made of moulded plastic, which reduces the cost of the inhaler.

Of course, it will be possible to make numerous modifications to the invention without departing from the scope thereof.

In particular, it will be possible for the mechanism for controlling the obturator 68 to be of a different structure. It will be possible for it to comprise an electronic sensor for detecting an under-pressure in the mouthpiece. It will be possible for the flap mechanism to be of a different type. It will be possible for the flap mechanism to form part of an inhaler of a different type, for example an inhaler with a strip of powder doses, an inhaler with a permanent store of compressed gas, or an aerosol inhaler.

It will be possible for the cells to have a cross-section decreasing downstream, without their shape necessarily being truncated. The characteristics concerning the shape of the cells may be applied to powder inhalers of different structures.

It will be possible for the positioning of the cells opposite the orifice to be controlled by separate means, independently of the compression of the chamber by the lever.

The principle of assembling certain components on a common support 10 before they are introduced into the casing may be applied to inhalers of different structures, for example aerosol inhalers. It will be possible for the components to be fixed to each other by means other than clipping.

It will be possible for the means controlling the compression of the chamber and/or the positioning of the cells to be other than a lever. It will be possible to use a knurled knob.

It will be possible to modify the number of groups of cells, and the number of cells in each group, as well as the arrangement of the cells in each group. To improve the fragmentation of the powder, it will be advantageous to reduce the surface area of the wall of the plate extending between the cells lying opposite the orifice 128 during use, either by increasing the number of cells and reducing their size, or else by reducing the diameter of the orifice 128 and placing the cells closer together. It will be possible to replace the disc of the plate with a grille, for example of a honeycomb structure in which the cells will constitute the powder-dosing cells.

In the above description, the inhaler includes means for returning the ratchet to a position in which it bears on the flap.

I claim:

1. Powder inhaler including a gas supply chamber, a conduit communicating with the chamber via an orifice and leading into an inhalation mouthpiece, means for bringing a dose of powder into the conduit, and a detector for detecting suction created in the mouthpiece, the powder inhaler additionally including a movable obturator configured to close off the orifice, the obturator being movable between an orifice closing position and an orifice opening position, a releasable immobilizing mechanism for holding the obturator in the orifice closing position, and a gas providing mechanism for providing compressed gas in the air supply chamber to discharge the powder through the mouthpiece when the orifice is open, the gas chamber communicating with the obturator whereby the compressed gas is able to bias the obturator toward the orifice opening position prior to the detection of suction in the mouthpiece by the detector, the immobilizing mechanism opposing the compressed gas to hold the obturator in the orifice closing position, the immobilizing mechanism being operably connected to the detector for releasing the obturator in response to the detection of suction in the mouthpiece, enabling the obturator to be immediately driven to the orifice opening position by the compressed gas.

2. Inhaler according to claim 1, characterized in that it includes a second conduit separate from the first conduit and communicating with the mouthpiece, the detector extending within the second conduit.

3. Inhaler according to claim 1, wherein the obturator is movable slidably in a channel communicating with the chamber, the orifice being formed in a lateral wall of the channel, the obturator making a leaktight connection with the channel.

4. Inhaler according to claim 1, wherein the detector includes a rotating flap designed to be rotated by suction in the mouthpiece.

5. Inhaler according to claim 4, wherein the distancing means includes a ratchet articulated on the obturator, the ratchet being designed to bear on the flap when the flap is in a rest position, and in such a way that the bearing is suppressed when the flap is set in rotation.

6. Inhaler according to claim 5, which includes means for returning the ratchet to a position in which it bears on the flap.

7. Inhaler according to claim 6, wherein the return means includes a flexible blade bearing on the obturator.

8. Inhaler according to claim 7, wherein the ratchet includes a wall having a recess, the blade being connected to an edge of the wall and extending in line with the recess.

9. Inhaler according to claim 5, wherein the ratchet includes a catch abutting against the obturator.

10. Inhaler according to claim 5, wherein the ratchet includes at least one sharp edge via which the ratchet bears on the flap.

11. Inhaler according to claim 10, wherein the flap includes a journal arranged to serve as a bearing for the edge.

12. Inhaler according to claim 1, wherein the compression chamber includes a piston, and the inhaler includes means for actuating the piston to bring the chamber into a compression state, these means being designed to prohibit actuation of the means by the piston when the chamber is in the compression state.

13. Inhaler according to claim 12, wherein the actuation means includes a lever.

* * * * *